(12) United States Patent
Heymans (10) Patent No.: US 12,203,067 B2
(45) Date of Patent: Jan. 21, 2025

(54) MIXTURE OF BRANCHED SECONDARY ALCOHOL ETHOXYLATES FOR REMOVAL OF ENDOTOXINS IN ANION EXCHANGE CHROMATOGRAPHY

(71) Applicant: Axagarius GmbH & Co. KG, Dueren (DE)

(72) Inventor: Stefan Heymans, Solingen (DE)

(73) Assignee: Axagarius GmbH & Co. KG, Dueren (DE)

( * ) Notice: Subject to any disclaimer, the term of this patent is extended or adjusted under 35 U.S.C. 154(b) by 56 days.

(21) Appl. No.: 17/833,675

(22) Filed: Jun. 6, 2022

(65) Prior Publication Data

US 2023/0016026 A1 Jan. 19, 2023

(30) Foreign Application Priority Data

Jul. 2, 2021 (EP) .................................... 21183538

(51) Int. Cl.
*C12N 15/10* (2006.01)
*B01D 15/36* (2006.01)
(Continued)

(52) U.S. Cl.
CPC ......... *C12N 15/101* (2013.01); *B01D 15/363* (2013.01); *C11D 1/72* (2013.01); *C11D 1/722* (2013.01); *C12N 1/06* (2013.01)

(58) Field of Classification Search
CPC ...... C12N 15/01; C12N 1/06; C12N 15/1006; C12N 15/101; B01D 15/363; C11D 1/72; C11D 1/722
See application file for complete search history.

(56) References Cited

U.S. PATENT DOCUMENTS

| 6,428,703 B1 * | 8/2002 | Zinn ...................... B01D 15/08 |
| | | 210/659 |
| 2004/0063597 A1 | 4/2004 | Adair et al. |
| 2014/0227712 A1 * | 8/2014 | Horlitz ................. C12Q 1/6806 |
| | | 536/25.4 |

FOREIGN PATENT DOCUMENTS

EP 2 963 158 A1 1/2016

OTHER PUBLICATIONS

Haruki, M. et al. "Measurement and modeling of the phase behavior of supercritical carbon dioxide + polydisperse non-ionic surfactant systems", 2009, Fluid Phase Equilibria, vol. 287, pp. 7-14. (Year: 2009).*

(Continued)

*Primary Examiner* — Eric Olson
*Assistant Examiner* — Benjamin M Brandsen
(74) *Attorney, Agent, or Firm* — Kilpatrick Townsend & Stockton LLP (57) ABSTRACT

Provided herein is a method to reduce the endotoxin contamination in plasmid preparations. In the described method, plasmid DNA and endotoxins are bound to an anionic exchange matrix and are brought into contact with a wash buffer, comprising a combination of branched secondary alcohol ethoxylates with varying ethylene oxide chain lengths, wherein the branched secondary alcohol ethoxylates with the shorter ethoxylate chain is present in the washing buffer in excess compared to the branched secondary alcohol ethoxylate with the longer ethoxylate chain. The resulting purified plasmid has minimal endotoxin contamination levels and is considered endotoxin-free. Furthermore, provided are wash buffers comprising a combination of branched secondary alcohol ethoxylates with varying ethylene oxide chain lengths, kits comprising such wash buffers and the use (Continued)

of such wash buffers for reducing the endotoxin contamination in plasmid preparations.

26 Claims, 4 Drawing Sheets

(51) Int. Cl.
   *C11D 1/72* (2006.01)
   *C11D 1/722* (2006.01)
   *C12N 1/06* (2006.01)

(56) References Cited

OTHER PUBLICATIONS

Budelier, K. et al. "Purification of DNA by Anion-Exchange Chromatography", 1998, Current Protocols in Molecular Biology, pp. 2.1.11-2.1.18. (Year: 1998).*
Certificate of Analysis, Tergitol TMN-6, Sigma-Aldrich. (Year: 2023).*
Certificate of Analysis, Tergitol TMN-10, Sigma-Aldrich. (Year: 2023).*
Safety Data Sheet, Buffer Wash, Macherey-Nagel, see Section 3: Composition/Information on Ingredients. (Year: 2022).*
Safety Data Sheet, Buffer Elu, Macherey-Nagel, see Section 3: Composition/Information on Ingredients. (Year: 2022).*
Dow Chemicals, Dow Surfactants—Alternatives to Alkyl Phenol Ethoxylate (APE, APEO) Surfactants.*
Florin, E.; et al. "Salt Effects on the Cloud Point of the Poly(ethylene oxide)+Water System" 1984, J. Chem. Soc. Faraday Trans., vol. 80, pp. 2889-2910. (Year: 1984).*
European Search Report dated Dec. 14, 2021 in related European Patent Application No. 21183538.4 (eight pages).
Ryoo Won, et al., "Water-in-Carbon Dioxide Microemulsions with Methylated Branched Hydrocarbon Surfactants," Industrial & Engineering Chemistry Research, vol. 42, No. 25, pp. 6348-6358 (Dec. 1, 2003).
"Detergents for nucleic acid purification in anion exchange chromatography", Research Disclosure, Kenneth Mason Publications, Hampshire, UK, GB, vol. 682, No. 31 (Jun. 1, 2021).
Dow, Technical Data Sheet Tergitol TMN-6 (90%) Surfactant Product Information; Form No. 119-01939-0817; 1 page.
Dow, Technical Data Sheet Tergitol TMN-10 (90%) Surfactant Product Information; Form No. 119-01934-1107; 2 pages.
Dow, Technical Data Sheet Tergitol TMN-3, Surfactant Product Information; Form No. 119-01938-1107.

* cited by examiner

MIXTURE OF BRANCHED SECONDARY ALCOHOL ETHOXYLATES FOR REMOVAL OF ENDOTOXINS IN ANION EXCHANGE CHROMATOGRAPHY

CROSS REFERENCES

The present application claims priority of EP21183538.4 filed 2 Jul. 2021, the disclosure of which is incorporated herein in its entirety.

SUMMARY OF THE INVENTION

Provided herein is a method to reduce the endotoxin contamination in plasmid preparations. In the described method, plasmid DNA and endotoxins are bound to an anionic exchange matrix and are brought into contact with a wash buffer, comprising a combination of branched secondary alcohol ethoxylates with varying ethylene oxide chain lengths, wherein the branched secondary alcohol ethoxylates with the shorter ethoxylate chain is present in the washing buffer in excess compared to the branched secondary alcohol ethoxylate with the longer ethoxylate chain. The resulting purified plasmid has minimal endotoxin contamination levels and is considered endotoxin-free. The use of branched secondary alcohol ethoxylates shows unexpected advantages over the linear primary or secondary alcohol ethoxylates, while the use of a combination of different branched secondary alcohol ethoxylates with different ethylene oxide chain lengths increases solubility and stability over a single branched secondary alcohol ethoxylate in anion exchange washing buffers with high ionic strength. The described method is cost effective, scalable and can be easily integrated into existing workflows. Furthermore, provided are wash buffers comprising a combination of branched secondary alcohol ethoxylates with varying ethylene oxide chain lengths, kits comprising such wash buffers and the use of such wash buffers for reducing the endotoxin contamination in plasmid preparations.

BACKGROUND OF THE INVENTION

Endotoxins show comparable purification characteristics to nucleic acids because of their structure as macromolecular and at least partially phosphorylated polysaccharides. They are major contaminants in plasmid preparations. Depending on the desired downstream application, endotoxins must be removed to a varying extend. While sequencing and cloning applications are not significantly biased by endotoxins, pharmaceutical downstream applications and the use of plasmid DNA in vivo require a stringent removal of endotoxins. To date, most plasmid purification procedures for pharmaceutical and sensitive applications employ an anion exchange (AX) chromatography step in the workflow, which is combined with additional techniques like hydrophobic interaction chromatography (HIC) to further reduce the amount of endotoxins. There is a need for a simple, scalable and inexpensive method to separate plasmid DNA from endotoxins on a nearly quantitative level.

The amount of contaminating endotoxins is usually referred to as endotoxin units per microgram DNA (EU/µg) and should be below 0.1 EU/µg for sensitive downstream applications. There are various in vivo and in vitro methods to quantify endotoxins. A commonly used method is the Limulus Amoebocyte Lysate test (LAL test) in various layouts. These test methods are described for example in US Pharmacopeial Convention, <85> Bacterial Endotoxin Test (2011), or Eu. Ph. 2.6.14 Bacterial Endotoxins and Q4B Annex 14 Step 3 Bacterial Endotoxins.

The use of detergents, including branched secondary alcohol ethoxylates, for nucleic acid purification is well known in the art, see e.g. Research Disclosure vol. 682(31), 1 Jun. 2021. EP1125943B1 describes the separation of plasmid DNA from endotoxins during anion exchange chromatography by use of a nonionic detergent from the polyethylene ether group, more precisely by detergents of the Triton® X group. This class, chemically 4-tert-octylphenol ethoxylates or, by another nomenclature, alkyl phenol ethoxylates (APE), was added to the REACH Annex XIV of the European Chemicals Agency (ECHA) with sunset date January 4th 2021 due to endocrine disrupting effects of degradation products in the environment. Continued use requires authorization and is undesirable due to the negative effects on especially aquatic ecosystems. 4-tert-octylphenol ethoxylates, especially Triton® X-114, have been the backbone of many described procedures in the literature dealing with the purification and separation of biomolecules like DNA, RNA or protein from endotoxins. Further examples of endotoxin removal strategies, based on Triton® X-114, include WO1995/021179A1 or Aida and Pabst, J. Immunol. Methods 132:191-195 (1990). There have been efforts to find alternatives for Triton® X on a general basis and in the context of nucleic acid purification. The manufacturer of Triton® X, Dow Chemicals published an overview ("Dow Surfactants—Alternatives to Alkyl Phenol Ethoxylate (APE, APEO) Surfactants") with suggestions of substitutes. In particular, it is suggested that Triton® X-114 should be substituted by Ecosurf® EH-6, Ecosurf® SA-7, Tergitol® 15-S-7 or Tergitol® TMN-6 (90%). As claimed within this cited literature, Tergitol® 15-S-7 is the suggested starting point. In the light of this recommendation, the publication "Detergents for nucleic acid purification in anion exchange chromatography", disclosed anonymously in Research Disclosure on 7 Jan. 2021, confirms that Tergitol® 15-S-7, an unbranched secondary alcohol ethoxylate, is a potent replacement for Triton® X in standard plasmid DNA purification applications. Nevertheless, the endotoxin concentration in this publication is higher than applicable for sensitive downstream applications. Secondary alcohol ethoxylates from the Tergitol 15-S-type exhibit an endotoxin concentration, which is several-fold higher than desired for pharmaceutical, in vivo and other endotoxin-sensitive applications, while primary alcohol ethoxylates of the Brij® series share this disadvantage to an increased extend and exhibit further technical disadvantages like reduced flow rates. Branched secondary alcohol ethoxylates of the Tergitol® TMN-type show increased endotoxin removal properties, but also interfere with the DNA purification, resulting in DNA loss. The authors state, that detergents with a short ethylene oxide chain length, such as Tergitol® TMN-3, TMN-6 and 15-S-3, form an emulsion rather than a solution in the tested washing buffers. A long-term stability of a wash buffer containing branched secondary alcohol ethoxylates with short ethylene oxide chains is unlikely. It is expected that a phase separation will lead to a separation of an aqueous phase and a detergent phase. Such a mixture is difficult to handle, and its application is error prone, rendering it inapplicable for sensitive and critical downstream applications, especially in a pharmaceutical environment. A mixture of detergents was not contemplated in this publication.

U.S. Pat. No. 7,531,308B2 and U.S. Pat. No. 6,617,443B2 both describe a pre-incubation of a solution containing DNA and endotoxins with a detergent solution before applying the mixture to a DNA binding matrix. Both patents share the disadvantage that an additional incubation step is necessary, especially limiting the scalability as the amount of lysate and thus the necessary volume of an incubation solution to achieve an effective concentration increases dramatically in a production scale.

EP 2963158 A1, WO 2004/0063597 A1 and W. Ryoo et al., Ind. Eng. Chem. Res. (42):6348-6358 (2003) disclose mixtures of Tergitol® detergents.

SUMMARY OF THE INVENTION

According to a first aspect of the invention (hereinafter shortly referred to as aspect (1)), provided is a method for purifying or isolating plasmid DNA and reducing the endotoxin contamination thereof, which comprises
(a) lysing bacterial cells containing the desired plasmid DNA;
(b) clearing the cell lysate from cell debris and precipitated contaminants;
(c) applying the cleared lysate to an anion exchange matrix, therewith binding DNA, endotoxins and other polyanions from the cleared lysate at least partially to the anion exchange matrix;
(d) washing the anion exchange matrix with an aqueous washing buffer comprising at least two different secondary branched alcohol ethoxylate detergents with different ethylene oxide (EO) chain length to remove endotoxins bound to the anion exchange matrix, wherein the amount (vol) of the secondary branched alcohol ethoxylate detergent with the shorter EO chain is greater than that of the secondary branched alcohol ethoxylate detergent with the longer EO chain;
(e) eluting the plasmid DNA from the anion exchange matrix with an elution buffer. The second aspect of the invention relates to a preferred embodiment of the method of aspect (1) of the invention, wherein, prior to step (c), the anion exchange matrix is equilibrated with an equilibration buffer comprising a detergent and/or an alcohol. In the third aspect of the invention, the equilibration buffer utilized in the method of aspect (2) comprises at least two different secondary branched alcohol ethoxylate detergents with different EO chain length, wherein the amount (vol) of the secondary branched alcohol ethoxylate detergent with the shorter EO chain is greater than that of the secondary branched alcohol ethoxylate detergent with the longer EO chain. The fourth aspect of the invention provides an aqueous wash buffer comprising at least two different secondary branched alcohol ethoxylate detergents with different EO chain length, wherein the amount (vol) of the secondary branched alcohol ethoxylate detergent with the shorter EO chain is greater than that of the secondary branched alcohol ethoxylate detergent with the longer EO chain.

The fifth aspect of the invention provides an equilibration buffer comprising two different secondary branched alcohol ethoxylate detergents with different ethylene oxide chain length, wherein the amount (vol) of the secondary branched alcohol ethoxylate detergent with the shorter EO chain is greater than that of the secondary branched alcohol ethoxylate detergent with the longer EO chain.

The sixth aspect of the invention provides for a kit comprising the aqueous wash buffer of aspect (4) of the invention and/or the equilibration buffer of aspect (5) of the invention.

The seventh aspect of the invention provides for the use of the aqueous wash buffer of aspect (4) of the invention for reducing endotoxin contamination in plasmid preparations.

SHORT DESCRIPTION OF THE FIGURES

FIGS. 2 A and B: Comparison of washing buffers with pure Tergitol® TMN-6 in A and a combination of Tergitol® TMN-6 and TMN-10 in B.

DETAILED DESCRIPTION OF THE INVENTION

Aspects (1) to (3) of the invention relate to an easy and scalable method to reduce the endotoxin concentration to levels, which are applicable for pharmaceutical and in vivo applications.

Plasmid DNA is propagated in bacterial cells, according to established methods known in the art. After the propagation, bacterial cells containing the desired plasmid DNA are separated from the culture broth by methods known in the art, for example by centrifugation or filtration. Bacterial cells are resuspended in a resuspension buffer, lysed with a lysis buffer, optionally incubated and neutralized with a neutralization buffer. The crude lysate is cleared from cell debris as well as from precipitated contaminants by methods known in the art, for example by filtration or by centrifugation. The cleared lysate is directly applied to an equilibrated anion exchange matrix where DNA and endotoxins as well as other polyanions bind at least partially to the anion exchange matrix.

In the method of aspects (1) to (3) of the invention the two branched secondary alcohol ethoxylate detergents may have the same branched $C_{8-18}$ alkane, preferably $C_{10}$-15 alkane with one secondary alcohol group as hydrophobic part and a linear polymeric EO chain of variable length attached to said alcohol as hydrophilic part. Moreover, the different EO chains of the detergents may have from 5 to 20 EO units.

In a preferred embodiment of the method of the invention, the two branched secondary alcohol ethoxylate detergents are compounds of the general formula (I)

(I)

wherein n represents the number of EO repetitions and is, independent from its occurrence in the other detergent, an integer from 5 to 20. It is particularly preferred that n is an integer from 6 to 15 and/or that the difference of n in the at least two detergents is at least 2, most preferably the difference of n is at least 3.

In a particularly preferred embodiment of the method of the invention, one of the secondary branched alcohol ethoxylate detergents is a compound of the general formula (I) with n=8 and the other is a compound of the general formula (I) with n=11.

In another preferred embodiment of the invention, in the wash buffer and/or the equilibration buffer, the ratio (v/v) of the detergent with a shorter EO chain to that with a longer EO chain is in the range from 10:1 to 1.5:1, preferably in the range of 5:1 to 2:1. Particularly preferred is that the detergent mixture is a combination of about 4 parts (vol) of the shorter chain detergent and 1 part (vol) of the longer chain detergent.

In another preferred embodiment of the invention, the wash buffer and/or the equilibration buffer comprises the detergent mixture in a concentration of at least 0.1% (v/v), preferably at least 0.5% (v/v). It is also preferred that the wash buffer further comprises at least one salt, preferably a salt selected from KCl, NaCl, LiCl, CaCl$_2$), MgCl$_2$, and corresponding acetates, in a concentration of at least 500 mM. Moreover, it is preferred that the wash buffer further comprises at least a buffer substance, preferably Tris, MOPS, Bis-Tris or phosphate, in a concentration sufficient to stabilize the pH value. Finally, it is also preferred that the wash buffer does only contain low amounts of organic solvents such as ethanol, or does not contain any organic solvents, such as ethanol.

In another preferred embodiment, the equilibration buffer of aspect (2) or (3) of the invention contains at least a buffer substance and is buffered to a pH which protonates the anion exchange groups of the anion exchange matrix, preferably the buffer substance is selected from Tris, MOPS, Bis-Tris and phosphate.

In another preferred embodiment of the method of aspects (1) to (3), after washing step (d), further comprises washing with a detergent-free aqueous wash buffer, preferably said aqueous wash buffer comprising at least one salt and a buffer substance, e.g. as defined in the detergent-containing wash buffer defined hereinbefore.

In another preferred embodiment of the method of aspects (1) to (3), the elution buffer comprises at least one salt and a buffer substance stabilizing an alkaline pH value. Suitable salts and buffer substances include as salts KCl, NaCl, LiCl, CaCl$_2$), MgCl$_2$, and corresponding acetates, and as buffer substances Tris, MOPS, Bis-Tris or phosphate.

The method of aspects (1) to (3) are well suited for reducing endotoxin contamination in plasmid preparations.

According to the invention, a first aqueous wash buffer, comprising a mixture of at least two different secondary branched alcohol ethoxylate detergents with different ethylene oxide chain lengths, removes the bound endotoxins. In a preferred embodiment, the detergent mixture of branched secondary alcohol ethoxylates is a mixture of at least a detergent with 8 moles EO and at least one detergent with 11 moles EO. The short-chained detergent is used in excess. In an additionally preferred embodiment, the detergent mixture is a combination of 4 parts (vol) of the short chain detergent and 1 part (vol) of the long chain detergent.

Plasmid DNA is eluted from the anion exchange matrix by an elution buffer after an optional second washing step with a second wash buffer, neither containing a detergent mixture as the first wash buffer, nor any other detergent. The eluted DNA is further concentrated and desalted by methods known in the art, for example by isopropanol precipitation.

Plasmid DNA is an extrachromosomal DNA molecule, which replicates independently from the host cell genome. Usually, plasmids are circular and covalently closed. Although plasmids originate from nature, modern artificial plasmids have been genetically modified to express desired features for biotechnological applications, which are known in the art. For example, plasmids are used to produce proteins or as a template for in vitro transcription. A major advantage of plasmids is their ability to self-replicate. A single bacterial cell can contain several hundred identical so-called high-copy plasmids, thus increasing the number of plasmids in a propagating bacterial cell culture. Depending on the plasmid type, cell culture volume and the cell titer, plasmid yields ranging from several micrograms up to several hundred milligrams are expected. The method of endotoxin reduction described herein can be adapted to all purification scales.

Endotoxins are a part of the cell wall of Gram-negative bacteria. Endotoxins are lipopolysaccharides, composed of a hydrophobic lipid moiety (Lipid A) and a hydrophilic polysaccharide, which is partially phosphorylated. Endotoxins usually co-purify with DNA, making them common contaminants in plasmid preparations. In vivo, the Lipid A moiety promotes a potentially fatal systemic immune reaction by activation of TLR-4 receptors. Applications in vivo and sensitive in vitro experiments require endotoxin-free solutions. Usually, the amount of endotoxins is specified as endotoxin units (EU) while the endotoxin concentration in plasmid preparations is usually specified as endotoxin units per microgram plasmid DNA (EU/μg). The endotoxin concentration can be determined by a chromogenic LAL test, which is an enzymatic reaction cascade, started by the presence of endotoxins. The final reaction step of a chromogenic LAL test cleaves a chromogenic substrate, thus enabling a quantification of the endotoxin concentration. This and alternative procedures for endotoxin tests are described for example in US Pharmacopeial Convention, <85> Bacterial Endotoxin Test (2011), or Eu. Ph. 2.6.14 Bacterial Endotoxins and Q4B Annex 14 Step 3 Bacterial Endotoxins. Plasmid DNA solutions are usually specified as endotoxin-free if the endotoxin concentration is below 0.1 EU/μg.

A resuspension buffer is an aqueous solution, which is used to resuspend a pellet of cells containing plasmid DNA. The resuspension buffer contains at least Ethylenediaminetetraacetic acid (EDTA) in a concentration ranging from 1 to 20 mmol/l (mM), preferred in a concentration of 8 to 12 mM. The resuspension buffer may contain further substances, for example a pH-indicator, at least one salt or a dye. Additionally, the resuspension buffer may contain a ribonuclease, preferred is Ribonuclease A (RNase A), in a concentration of 50 to 500 μg/ml. The resuspension buffer may be buffered to a neutral to slightly alkaline pH value of pH 7 to 9. Preferred value is pH 8.

A lysis buffer is an aqueous solution, which is used to release the plasmid DNA from within the bacterial cells. According to a modified alkaline lysis, the lysis buffer contains sodium dodecyl sulfate in a concentration ranging from 0.2 to 2% (m/v) and sodium hydroxide in a concentration ranging from 150 to 1000 mM. The lysis buffer may contain supplementary substances like a pH indicator or a dye. Lysis buffers for Gram-positive bacteria may contain cell wall degrading enzymes like lysozyme instead.

A neutralization buffer is an aqueous solution, which is used to neutralize the alkaline pH value of the lysate. It contains at least an acidic buffer, preferred is acetic acid, in concentrations sufficient to adjust the pH value of the combined lysate solution to a neutral to acidic pH value. In addition, the neutralization buffer contains potassium ions in excess to the dodecyl sulfate from the lysis buffer, enabling a quantitative precipitation of insoluble potassium dodecyl sulfate. The neutralization buffer may contain further supplementary substances like a pH-indicator or a dye and at least one further salt.

Methods to remove the precipitates from the crude lysates include filtration and/or centrifugation steps and are well known in the art. An example is the use of filter disks, folded filters or extraction thimbles of a suitable material, for example cellulose or glass fiber. Another example is sterile filtration with membranes of a pore size ranging from 0.2 to 0.45 μm, optionally designed as stepped filters with additional filter layers. A further example is centrifugation. The methods can be combined. It is state of the art to pre-wet filters. For this purpose, any suitable solution can be used, including the endotoxin removal buffer according to the invention described herein. An equilibration buffer is used to enable a binding of DNA to the anion exchange matrix. The equilibration buffer contains at least a buffer substance and is buffered to a pH which protonates the anion exchange groups of the anion exchange matrix, in case of a tertiary amine. The equilibration buffer contains a detergent and/or an alcohol in order to overcome the phase separation between the solid phase (anion exchange matrix, hydrophobic) and the liquid phase (lysate, wash buffers, hydrophilic). The used detergent may be the detergent mixture as present in the wash buffer as described hereinbefore in order to limit the number of different buffers and thus to prevent a potentially fatal buffer mix-up.

The anion exchange matrix may be fibrous or particulate. The core material is not relevant. In the art, cellulose or silica are examples for commonly used core materials due to well-established procedures for their chemical modification. The core material is modified by chemical groups, which exhibit either a constant positive charge, so called strong anion exchange resins, for example quaternary amines, or a conditional positive charge, so called weak anion exchange resins, for example tertiary amines. Well-known examples used in the art are for example diethylaminoethanol (DEAE) or methylaminothanol (MEA). Both are weak anion exchange residues and share the advantage that the presence of the positive charge is depending on the pH value of the surrounding solution. At acidic pH values, both groups exhibit a positive charge and will bind the constantly polyanionic nucleic acids, while at alkaline pH values the charge is absent, resulting in a release of the nucleic acid from the matrix. The anion exchange matrix can be used for example as a batch in solution, coupled to paramagnetic particles, as a packed bed within a chromatography column or as a filter disk.

A branched secondary alcohol ethoxylate is a molecule with a hydrophobic and a hydrophilic part. The hydrophobic part, according to the invention described herein, preferably is a branched $C_{12}$ alkane with one secondary alcohol group. This alcohol group is prolonged into to the hydrophilic part, a linear polymeric ethylene oxide (EO) chain of variable repetition number. Examples of commercially available branched secondary alcohol ethoxylates of the desired structure are Tergitol® TMN-6 with 8 moles of EO and Tergitol® TMN-10 with 11 moles of EO. The preferred branched secondary alcohol ethoxylate used in the detergent mixture of the invention has the general formula (I) below with n as the number of EO repetitions:

(I)

The detergent with the short EO chain preferably has n=8 (e. g., Tergitol® TMN-6) while the long-chained detergent has n=11 (e. g., Tergitol® TMN-10).

The detergent mixture, according to the invention described herein, is a mixture of secondary branched alcohol ethoxylates in a ratio (v/v) which is at least 2:1, preferred 3:1, even more preferred 4:1 with the larger part being the short-chained ethylene oxide residue. This detergent mixture is part of an aqueous washing solution in a concentration of at least 0.1 percent (v/v), preferred at least 0.5%.

The washing solution containing the detergent mixture further comprises at least one salt, e.g. lithium, natrium, potassium, magnesium or calcium, each as a chloride or acetate in a concentration of at least 500 mM.

The washing solution containing the detergent mixture further comprises at least a buffer substance, e.g. Tris, MOPS, Bis-Tris or phosphate in a concentration sufficient to stabilize the pH value.

The washing solution containing the detergent mixture does preferably not contain any organic solvents such as ethanol. This is relevant as washing solutions with Triton® X-114 generally contain about 15% ethanol, which is detrimental as such ethanol-containing detergent mixtures are subject to regulatory procedure and must be identified and render a hazardous material. Refraining from ethanol in the in the detergent mixture is therefore a technical advantage and further distinguishes the mixture over the art.

An optional second aqueous washing solution contains at least one salt and a buffer substance.

The elution solution contains at least one salt and a buffer substance stabilizing an alkaline pH value.

Concerning preferred embodiments of the wash and equilibration buffers of aspects (4) and (5), respectively, of the kit of aspect (6) and of the use of aspect (7) it is referred to the discussion of aspects (1) to (3) above. Moreover, the kit of aspect (6), if solely comprising the wash buffer of aspect (5), may further comprise an equilibration buffer as defined in aspect (2) of the invention, namely an equilibration buffer comprising a detergent and/or an alcohol (in a preferred embodiment of such kit, the equilibration buffer is then the equilibration buffer of aspect (5)), a detergent-free aqueous wash buffer, an elution buffer, a lyse buffer, and/or an anion exchange matrix s defined hereinbefore. The wash and equilibration buffers of aspects (4) and (5), respectively, and the kit of aspect (6) are particularly suited for performing the methods of aspects (1) to (3). The invention is further explained in the following examples, which are not to be construed as limiting the invention.

EXAMPLES

Example 1

*Escherichia coli* strain DH5α (Thermo Fisher Scientific) was transfected with the plasmid pcDNA™3.1 (+) (Thermo Fisher Scientific). The transfected cells were incubated overnight at 37° C. with constant shaking at 180 rpm in Cirglegrow™ medium (MP Biomedicals), containing 50 µg/ml Ampicillin (Sigma-Aldrich). Bacteria from 750 ml cell culture (absorption at 600 nm=9) were harvested by centrifugation at 5,000×g for 5 min at 4° C.

The bacterial cell pellet was resuspended in 135 ml resuspension buffer (50 mM Tris-CI, pH 8.0, 200 mM NaCl, 10 mM EDTA, 60 µg/ml RNase A) by vigorous vortexing. To the homogeneous suspension, 135 ml lysis buffer (200 mM sodium hydroxide, 1% sodium dodecyl sulfate) were added and mixed with the resuspended cells by inverting the flask until a homogeneous, viscous lysate was obtained. The mixture was incubated for 5 min at room temperature (21° C.) before 135 ml neutralization buffer (3000 mM potassium acetate, 1000 mM sodium chloride, adjusted to pH 5) were added. The resulting mixture was inverted until a homogeneous off-white precipitate had formed. The crude lysate was cleared by filtration with a Bottle Top Filter Type 2 (MACHEREY-NAGEL), yielding 360 ml of a cleared and pooled master-lysate.

NucleoBond® Xtra Midi Columns (MACHEREY-NAGEL, anion exchange columns with MAE-modified silica) including an extraction thimble were equilibrated with 12 ml of a washing (equilibration) buffer according to Table 1 in triplicate. The anion exchange columns were allowed to empty by gravity flow for all steps.

TABLE 1

Composition of washing buffer 1. The total detergent concentration is 0.5% throughout the experiment. The ratio of Tergitol ® TMN-6 (EO n = 8) to Tergitol ® TMN-10 (EO n = 11) is decreasing from 10:0 (v/v) to 0:10 (v/v). Triton ® X-100 and X-144 are used as reference.

| Buffer | Detergent | Buffer | Salt | Ethanol |
|---|---|---|---|---|
| 1 | 0.5% Tergitol ® TMN-6, 0.0% Tergitol ® TMN-10 | 100 mM Tris, pH 6.5 | 1.2M KCl | 15% |
| 2 | 0.4% Tergitol ® TMN-6, 0.1% Tergitol ® TMN-10 | 100 mM Tris, pH 6.5 | 1.2M KCl | 15% |
| 3 | 0.3% Tergitol ® TMN-6, 0.2% Tergitol ® TMN-10 | 100 mM Tris, pH 6.5 | 1.2M KCl | 15% |
| 4 | 0.2% Tergitol ® TMN-6, 0.3% Tegitol ® TMN-10 | 100 mM Tris, pH 6.5 | 1.2M KCl | 15% |
| 5 | 0.1% Tergitol ® TMN-6, 0.4% Tegitol ® TMN-10 | 100 mM Tris, pH 6.5 | 1.2M KCl | 15% |
| 6 | 0.0% Tergitol ® TMN-6, 0.5% Tegitol ® TMN-10 | 100 mM Tris, pH 6.5 | 1.2M KCl | 15% |
| 7 | 0.5% Triton ® X-100 | 100 mM Tris, pH 6.5 | 1.2M KCl | 15% |
| 8 | 0.5% Triton ® X-114 | 100 mM Tris, pH 6.5 | 1.2M KCl | 15% |

Once the washing (equilibration) buffer had passed the column completely, 15 ml of the cleared lysate were added to each column. Following that loading step, the columns were washed with each 5 ml of the corresponding washing (equilibration) buffer according to table 1. Once the washing (equilibration) buffer had passed the column completely, 8 ml of a second washing buffer (100 mM Tris, pH 7.0, 1.2 M potassium chloride, 15% ethanol) were added to each column. Plasmid DNA was eluted by addition of 5 ml elution buffer (100 mM Tris, pH 9.0, 1.2 M potassium chloride, 15% isopropanol) to each column. The column flow through was collected individually for each column and precipitated by addition of 0.7 volumes isopropanol. The samples were mixed by vortexing, incubated for 2 min at room temperature (21° C.) and centrifuged at 4° C. for 15 min at 5,000×g. The supernatant was decanted and the DNA pellets washed with 2 ml of 70% ethanol each. After another centrifugation step (5 min with 5,000×g at 4° C.), the supernatant was decanted and the DNA pellet dried at room temperature. Once the ethanol was evaporated completely, each DNA pellet was redissolved in 500 µl endotoxin-free $H_2O$-EF (MACHEREY-NAGEL).

The redissolved DNA was measured photometrically (230 nm, 260 nm, 280 nm). The purity ratios A260/A230 and A260/A280 and the DNA-concentration (according to the A260) were calculated. 1 µl of the redissolved DNA was loaded onto a 1% TAE Agarose gel which was run for 60 min at 100 V. 50 µl of the undiluted eluates were used in a chromogenic LAL test (Associates of Cape Cod, Pyrochrome). Endotoxin concentrations were calculated according to the standard curves with the corresponding Control Standard Endotoxine (Associates of Cape Cod, CSE).

Table 2 shows the photometric results. There is no obvious difference between the detergent combinations: all combinations result in values, which are regarded as indicators for pure DNA (A260/A230: 1.9 to 2.4, A260/A280: 1.8 to 1.9).

TABLE 2

Summary of the results from experiment 1. The ratio of the absorption from 260 nm by 230 nm and from 260 nm to 280 nm show no difference between the detergent combinations and indicate pure DNA. The DNA yield is comparable for all combinations. Endotoxin units per microgram DNA show a minimum at an 8:2 ratio of Tergitol ® TMN-6 to TMN-10 with an increase in both surrounding areas. The above line are the values of the triplicates, the bold figures in the lines below show the average value.

| Buffer | TMN-6:TMN-10 | A260/A230 | | | A260/A280 | | | yield (DNA)/µg | | | EU/µg | | |
|---|---|---|---|---|---|---|---|---|---|---|---|---|---|
| 1 | 10:0 | 2.35 | 2.35 | 2.35 | 1.88 | 1.85 | 1.88 | 179 | 152 | 154 | 0.063 | 0.010 | 0.016 |
|  |  |  | 2.35 |  |  | 1.87 |  |  | 162 |  |  | 0.029 |  |
| 2 | 8:2 | 2.37 | 2.35 | 2.34 | 1.83 | 1.89 | 1.88 | 169 | 162 | 161 | 0.005 | 0.012 | 0.010 |
|  |  |  | 2.35 |  |  | 1.87 |  |  | 164 |  |  | 0.009 |  |
| 3 | 6:4 | 2.29 | 2.37 | 2.36 | 1.75 | 1.85 | 1.87 | 154 | 169 | 151 | 0.007 | 0.014 | 0.012 |
|  |  |  | 2.34 |  |  | 1.82 |  |  | 158 |  |  | 0.011 |  |
| 4 | 4:6 | 2.27 | 2.36 | 2.36 | 1.83 | 1.86 | 1.87 | 161 | 157 | 154 | 0.020 | 0.020 | 0.016 |
|  |  |  | 2.33 |  |  | 1.85 |  |  | 157 |  |  | 0.019 |  |
| 5 | 2:8 | 2.35 | 2.27 | 2.36 | 1.87 | 1.78 | 1.87 | 155 | 166 | 156 | 0.027 | 0.031 | 0.020 |
|  |  |  | 2.33 |  |  | 1.84 |  |  | 159 |  |  | 0.026 |  |

TABLE 2-continued

Summary of the results from experiment 1. The ratio of the absorption from 260 nm by 230 nm and from 260 nm to 280 nm show no difference between the detergent combinations and indicate pure DNA. The DNA yield is comparable for all combinations. Endotoxin units per microgram DNA show a minimum at an 8:2 ratio of Tergitol ® TMN-6 to TMN-10 with an increase in both surrounding areas. The above line are the values of the triplicates, the bold figures in the lines below show the average value.

| Buffer | TMN-6:TMN-10 | A260/A230 | | | A260/A280 | | | yield (DNA)/µg | | | EU/µg | | |
|---|---|---|---|---|---|---|---|---|---|---|---|---|---|
| 6 | 0:10 | 2.34 | 2.29 | 2.32 | 1.85 | 1.80 | 1.88 | 165 | 151 | 159 | 0.042 | 0.041 | 0.040 |
|  |  |  | 2.32 |  |  | 1.84 |  |  | 158 |  |  | 0.041 |  |
| 7 | Triton ® X-100 | 2.36 | 2.37 | 2.30 | 1.88 | 1.88 | 1.88 | 156 | 138 | 163 | 0.013 | 0.015 | 0.047 |
|  |  |  | 2.34 |  |  | 1.88 |  |  | 153 |  |  | 0.025 |  |
| 8 | Triton ® X-114 | 2.30 | 2.37 | 2.27 | 1.86 | 1.87 | 1.85 | 136 | 149 | 151 | 0.025 | 0.018 | 0.027 |
|  |  |  | 2.31 |  |  | 1.86 |  |  | 145 |  |  | 0.023 |  |

Figure 1:
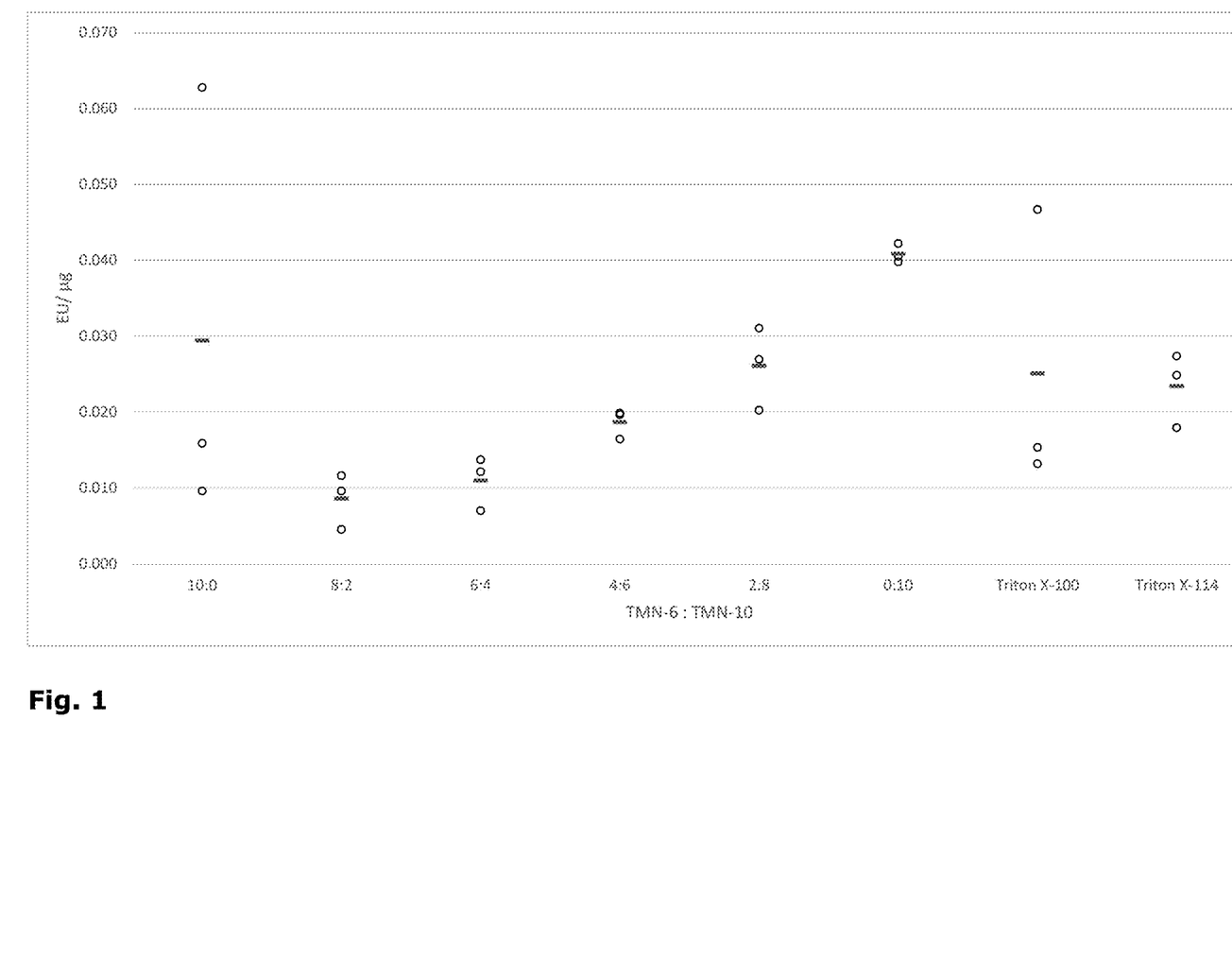
FIG. 1: Increasing EU/µg values with increasing percentage of Tergitol® TMN-10 but highly inhomogeneous values with pure Tergitol® TMN-6.

The only but striking difference in these results is the trend in the endotoxin units per microgram DNA. The EU/µg values show an increasing value with a higher percentage of long chained Tergitol® TMN-10 but do not steadily decrease towards the short-chained Tergitol® TMN-6. Surprisingly, pure Tergitol® TMN-6 as detergent within the washing buffer results in higher and inhomogeneous EU/µg values. This effect is clearly visible in FIG. 1.

Figure 2A:
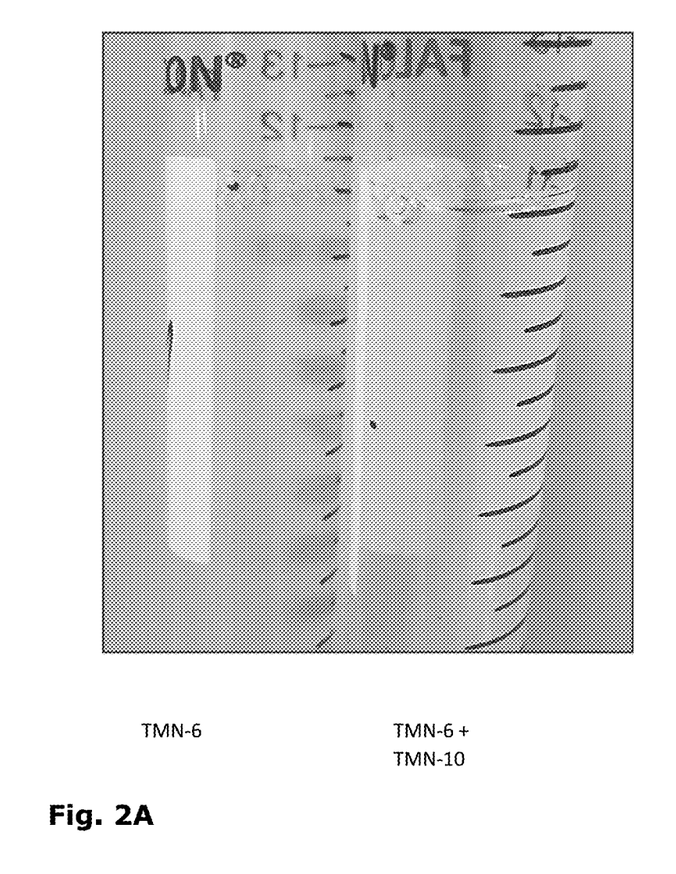
Figure 2B:
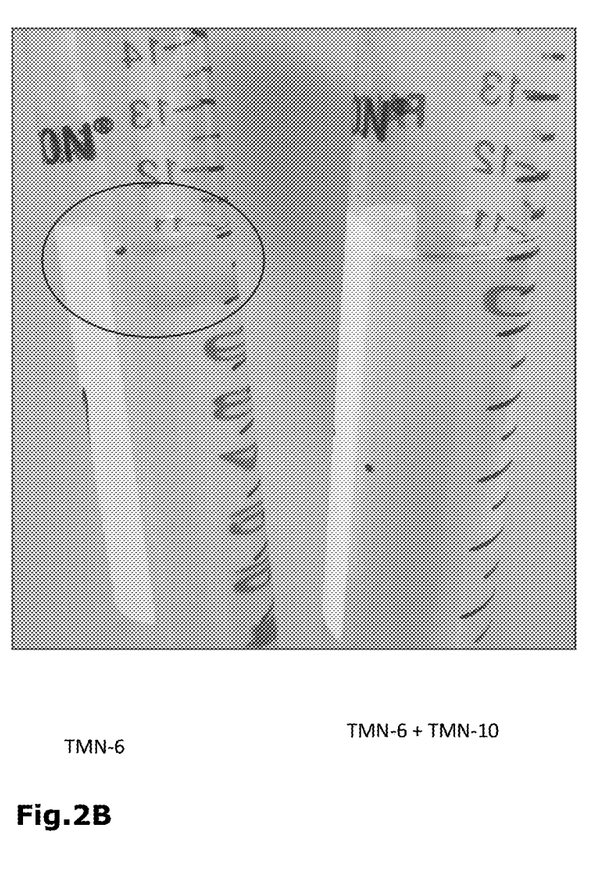

A likely explanation for this observation is that the detergent mixture #1 with 0.5% Tergitol® TMN-6 and without TMN-10 (10:0) was no solution but rather a turbid emulsion. FIG. 2A shows the difference between mixture #1 and mixtures #2 immediately after formulation. FIG. 2B shows the same solutions after an incubation time of 24 h in an upright position.

FIGS. 2A and 2B show a comparison of washing buffers with pure Tergitol® TMN-6 in A and a combination of Tergitol® TMN-6 and TMN-10 in B. The washing buffer with TMN-6 only is clearly turbid, indicating an emulsion. Addition of as little as 0.1% Tergitol® TMN-10 increases the solubility.

The turbidity, indicating an emulsion, is clearly visible for solution #1 with Tergitol® TMN-6 only. Consequently, a phase separation rapidly occurs with the organic (detergent) phase collecting at the top. Using an emulsion instead of a solution is problematic and will result in inhomogeneous results. Addition of as little as 0.1% (v/v) of Tergitol® TMN-10 results in a clear solution of the detergents, even in an aqueous buffer with a high salt concentration. The mixture remains to be a stable solution.

Figure 3:
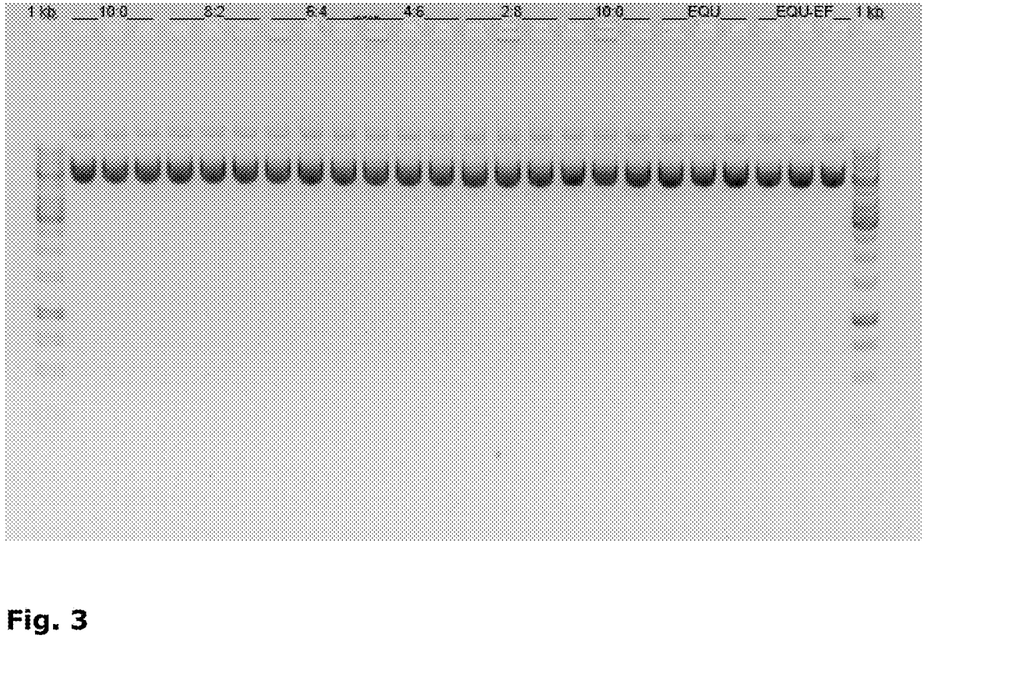
FIG. 3: Agarose gel image of the isolated plasmid DNA of Example 1.

FIG. 3 shown the result of the agarose gel analysis, showing no difference in plasmid band intensity or conformation. RNA or bacterial genomic DNA are not visible. FIG. 3 shows an agarose gel image of the isolated plasmid DNA. There is no obvious difference in band intensity, migration speed, ration of supercoiled plasmid DNA compared to other conformations and no detectable bacterial genomic DNA.

Example 2

*Escherichia coli* strain DH5a (Thermo Fisher Scientific) was transfected with the plasmid pcDNA™3.1 (+) (Thermo Fisher Scientific). The transfected cells were incubated overnight at 37° C. with constant shaking at 180 rpm in Cirglegrow™ medium (MP Biomedicals), containing 50 µg/ml Ampicillin (Sigma-Aldrich). Bacteria from 1500 ml cell culture (absorption at 600 nm=12.4) were harvested by centrifugation at 5,000×g for 5 min at 4° C.

The bacterial cell pellet was resuspended in 390 ml resuspension buffer (50 mM Tris-Cl, pH 8.0, 10 mM EDTA, 100 µg/ml RNase A) by vigorous vortexing. To the homogeneous suspension, 390 ml lysis buffer (200 mM sodium hydroxide, 1% sodium dodecyl sulfate) were added and mixed with the resuspended cells by inverting the flask until a homogeneous, viscous lysate was obtained. The mixture was incubated for 5 min at room temperature (21° C.) before 390 ml neutralization buffer (3000 mM potassium acetate, 1000 mM sodium chloride, adjusted to pH 5 with acetic acid) were added. The resulting mixture was inverted until a homogeneous off-white precipitate had formed. The crude lysate was cleared by filtration with a Bottle Top Filter Type 2 (MACHEREY-NAGEL), yielding 1000 ml of a cleared and pooled master-lysate.

A ChromaBond® Flash DL4 cartridge (MACHEREY-NAGEL) was filled with 3600 mg NucleoBond® Xtra anion exchange matrix (MACHEREY-NAGEL), contained between two polyethylene filter frits. The buffers mentioned in Table 3 below were passed through the filled ChromaBond® DL4 Flash column at a flow rate of constantly 4 ml/min. The flow was sustained by a peristaltic pump (Heidolph Hei-FLOW Precision 01, pump head SP standard) and a PharMed BPT 1/16" tubing (Saint-Gobain). The column flow through of each step, excluding the equilibration step, was collected in aliquots of 25 ml.

TABLE 3

Succession and essential composition of the solutions utilized in the experiment.

| Step | Detergent | Buffer | Salt | Function | Volume |
|---|---|---|---|---|---|
| 1 | 0.5% Tergitol ® TMN-6, 0.0% Tergitol ® TMN-10 | 100 mM Tris, pH 6.5 | 1.2M KCl | equilibration buffer | 1 × 15 ml |
| 2 | Pooled master-lysate | | | DNA loading | 22 × 25 ml |
| 3 | 0.3% Tergitol ® TMN-6, 0.2% Tergitol ® TMN-10 | 100 mM Tris, pH 6.5 | 1.2M KCl | Endotoxin removal | 2 × 25 ml |
| 4 | | 100 mM Tris, pH 7.0 | 1.2M KCl | General washing | 2 × 25 ml |
| 5 | | 100 mM Tris, pH 9.0 | 1.2M KCl | Elution | 8 × 25 ml |

Each flow through aliquot was precipitated by addition of 0.7 volumes isopropanol. The samples were mixed by vortexing, incubated for 2 min at room temperature (21° C.) and centrifuged at 4° C. for 15 min at 5,000×g. The supernatant was decanted and the DNA pellets washed with 2.5 ml of 70% ethanol each. After another centrifugation step (5 min with 5,000×g at 4° C.), the supernatant was decanted and the DNA pellet dried at room temperature.

Once the ethanol was evaporated completely, each DNA pellet was redissolved in 2 ml of endotoxin-free H₂O-EF (MACHEREY-NAGEL).

The redissolved samples were measured photometrically (230 nm, 260 nm, 280 nm). The purity ratios A260/A230 and A260/A280 and the DNA-concentration (according to the A260) were calculated for those samples expected to contain DNA (verified by the agarose gel analysis).

Figure 4:
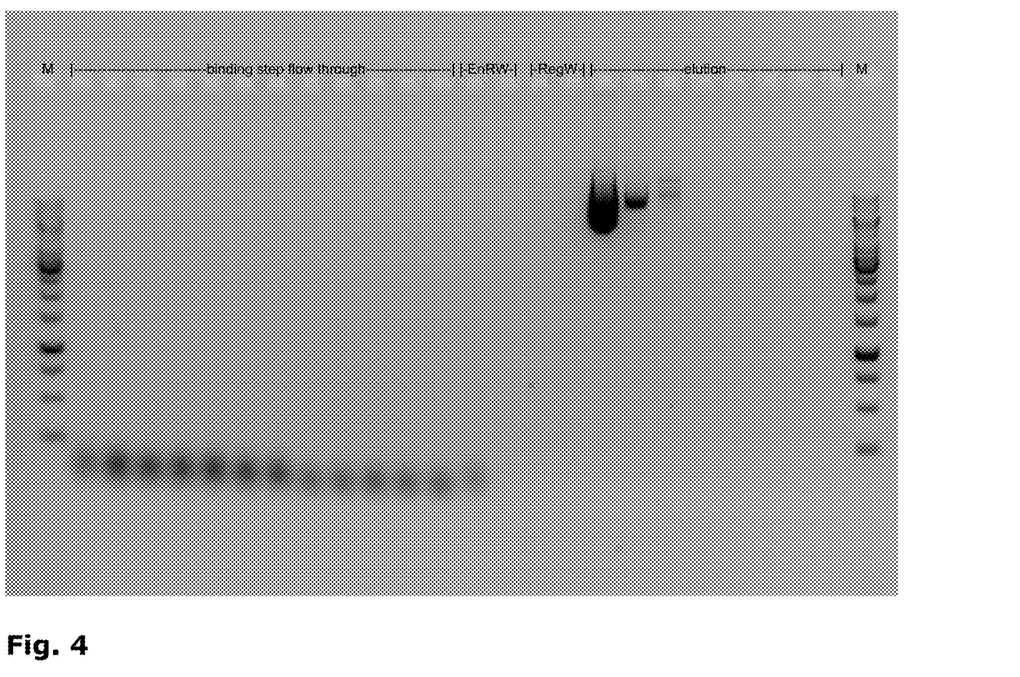
FIG. 4: Agarose gel analysis results of Example 2. Content of the flow through fractions. M=marker (GeneRuler 1 kb, Thermo Fisher Scientific), EnRW=endotoxin removal wash (with the described detergent mixture), RegW=regular wash, elution=elution step aliquots.

1 μl of the redissolved DNA was loaded onto a 1% TAE Agarose gel that was run for 60 min at 100 V. The samples were further analyzed in a chromogenic LAL test (Associates of Cape Cod, Pyrochrome). To ensure a measured value within the range of the Control Standard Endotoxin for each sample in the same measurement, samples were diluted from 1:1 (undiluted) to 1:10,000,000 with endotoxin-free H₂O-EF (MACHEREY-NAGEL). Endotoxin concentrations were calculated according to the standard curves with the corresponding Control Standard Endotoxine (Associates of Cape Cod, CSE). Values within the middle range of the calibration curve were used for endotoxin quantification. Protein concentration was measured with a Micro BCA test (Pierce). FIG. 4 shows the agarose gel analysis results.

The signal at low fragment lengths, visible in the binding step and the first endotoxin removal washing step, is hydrolyzed RNA, which did not bind to the anion exchange matrix. Desired plasmid DNA is only visible in the eluates, concentrated in the first elution fraction. Endotoxins are generally not visible on an ethidiumbromide-stained agarose gel. Table 4 shows the results of the quantification analysis.

TABLE 4

Results of the flow through analysis. The depicted values for binding and washing steps are average figures. The elution analysis is for elution step 1 only, as the other fractions do not contain DNA.

| Analysis | Binding | Endotoxin Removal Wash | Regular Wash | Elution (1) |
|---|---|---|---|---|
| Yield (DNA) | — | — | — | 5650 μg |
| EU/ml | 1845 | 16269 | 7 | 19 |
| EU/μg | — | — | — | 0.003 |
| A260/A230 | — | — | — | 2.3 |
| A260/A280 | — | — | — | 1.8 |
| Yield (protein) | 66 μg | 145 μg | 3 μg | 2 μg |

DNA was isolated in elution fraction 1 with high purity, sufficient for pharmaceutical and other sensitive downstream applications. It is obvious, that endotoxins have bound to the anion exchange matrix and were removed predominantly by the endotoxin wash solution according to the invention, as well as proteins. It is notable that endotoxins show a higher tendency than RNA to bind to an anion exchange matrix and are removed predominantly only by the endotoxin removal washing step.

Example 3

*Escherichia coli* strain DH5α (Thermo Fisher Scientific) was transfected with the plasmid pcDNA™3.1 (+) (Thermo Fisher Scientific). The transfected cells were incubated overnight at 37° C. with constant shaking at 180 rpm in Cirglegrow™ medium (MP Biomedicals), containing 50 μg/ml Ampicillin (Sigma-Aldrich). Bacteria from 500 ml cell culture (absorption at 600 nm=10) were harvested by centrifugation at 5,000×g for 5 min at 4° C.

The bacterial cell pellet was resuspended in 100 ml resuspension buffer (50 mM Tris-CI, pH 8.0, 10 mM EDTA, 100 μg/ml RNase A) by vigorous vortexing. To the homogeneous suspension, 100 ml lysis buffer (200 mM sodium hydroxide, 1% sodium dodecyl sulfate, 0.01% thymolphthaleine) were added and mixed with the resuspended cells by inverting the flask until a homogeneous, viscous lysate was obtained. The mixture was incubated for 5 min at room temperature (21° C.) before 100 ml neutralization buffer (3000 mM potassium acetate, adjusted to pH 5.5) were added. The resulting mixture was inverted until a homogeneous off-white precipitate had formed and the color of the pH-indicator was completely reverted. The crude lysate was cleared by centrifugation at 5,000×g for 5 min at 4° C. The clear supernatant was transferred to a clean flask.

NucleoBond® AX 100 columns (MACHEREY-NAGEL), anion exchange columns with MAE-modified silica) were equilibrated with 2.5 ml of washing buffers according to Table 5 in triplicate. The anion exchange columns were allowed to empty by gravity flow for all steps.

TABLE 5

Washing and equilibration buffers used in triplicate. Secondary branched alcohol ethoxylates (TMN-type) are mixed with unbranched secondary alcohol ethoxylates (15-S-type). The ratio of TMN-6 to TMN-10 remains constant at 0.4%:0.1% while the additional Tergitol ® 15-S-7 decreases in concentration from 0.5% to 0.0%. Buffer #1 is without the branched secondary alcohol ethoxylate mixture according to the invention.

| Buffer | Detergent | Buffer | Salt |
|---|---|---|---|
| 1 | 0.5% Tergitol ® 15-S-7, | 100 mM Tris, pH 6.5 | 1.2M KCl |
| 2 | 0.5% Tergitol ® 15-S-7, 0.4% Tergitol ® TMN-6, 0.1% Tergitol ® TMN-10 | 100 mM Tris, pH 6.5 | 1.2M KCl |
| 3 | 0.4% Tergitol ® 15-S-7, 0.4% Tergitol ® TMN-6, 0.1% Tergitol ® TMN-10 | 100 mM Tris, pH 6.5 | 1.2M KCl |
| 4 | 0.3% Tergitol ® 15-S-7, 0.4% Tergitol ® TMN-6, 0.1% Tegitol ® TMN-10 | 100 mM Tris, pH 6.5 | 1.2M KCl |
| 5 | 0.2% Tergitol ® 15-S-7, 0.4% Tergitol ® TMN-6, 0.1% Tegitol ® TMN-10 | 100 mM Tris, pH 6.5 | 1.2M KCl |
| 6 | 0.1% Tergitol ® 15-S-7, 0.4% Tergitol ® TMN-6, 0.1% Tegitol ® TMN-10 | 100 mM Tris, pH 6.5 | 1.2M KCl |
| 7 | 0.4% Tergitol ® TMN-6, 0.1% Tegitol ® TMN-10 | 100 mM Tris, pH 6.5 | 1.2M KCl |
| 8 | 0.5% Triton ® X-114 | 100 mM Tris, pH 6.5 | 1.2M KCl |

Table 5: Washing and equilibration buffers used in triplicate. Secondary branched alcohol ethoxylates (TMN-type) are mixed with unbranched secondary alcohol ethoxylates (15-S-type). The ratio of TMN-6 to TMN-10 remains constant at 0.4%: 0.1% while the additional Tergitol® 15-S-7 decreases in concentration from 0.5% to 0.0%. Buffer #1 is without the branched secondary alcohol ethoxylate mixture according to the invention.

Figure 5:
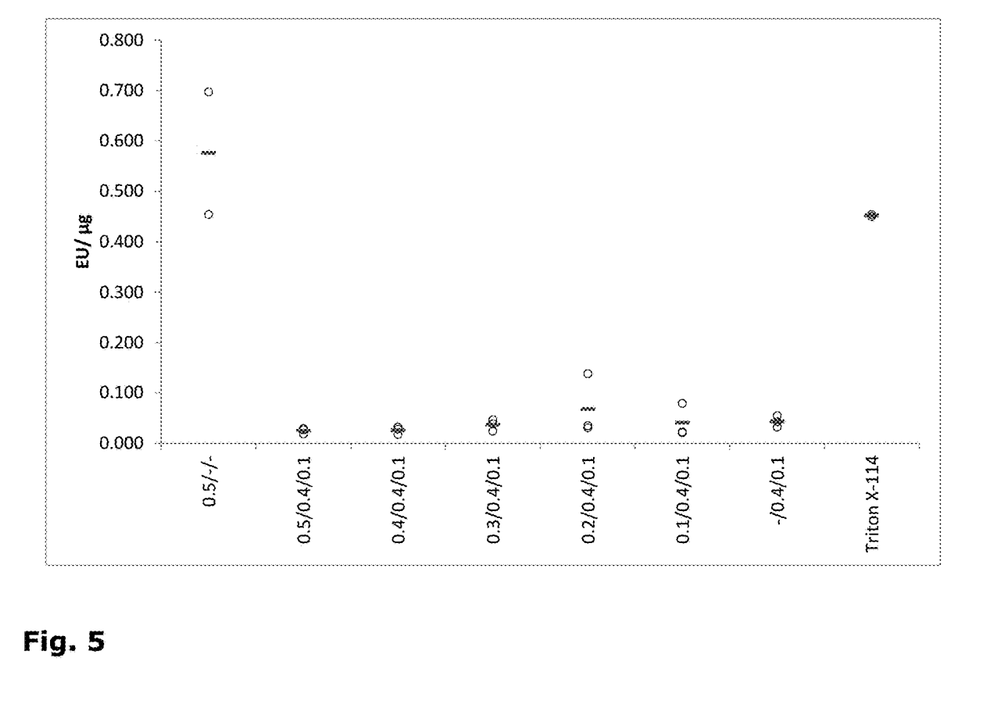
FIG. 5: Endotoxin concentration depending on the used equilibration and wash buffers. The x-axis is the percentage of the detergents Tergitol® 15-S-7/TMN-6/TMN-10 where 15-S-7 is an unbranched secondary alcohol ethoxylate and TMN is a branched secondary alcohol ethoxylate with TMN-6 and TMN-10 of varying ethyleneoxyde chain lengths.

10 ml of the pooled lysate was loaded into each equilibrated column. The columns were washed with 10 ml each of the washing buffer already used for equilibration according to table 5, followed by a second washing step with a detergent-free washing buffer (1.15 M potassium chloride, 100 mM Tris, pH 6.3, 15% ethanol). DNA was eluted from the anion exchange matrix with an elution buffer (100 mM Tris, pH 7, 1.5 M KCl, 15% ethanol). The column flow through was collected individually for each column and precipitated by addition of 0.7 volumes isopropanol. The samples were mixed by vortexing, incubated for 2 min at room temperature (21° C.) and centrifuged at 4° C. for 15 min at 5,000×g. The supernatant was decanted and the DNA pellets washed with 2 ml of 70% ethanol each. After another centrifugation step (5 min with 5,000×g at 4° C.), the supernatant was decanted and the DNA pellet dried at room temperature. Once the ethanol was evaporated completely, each DNA pellet was redissolved in 200 μl endotoxin-free H$_2$O-EF (MACHEREY-NAGEL). The redissolved DNA was measured photometrically (230 nm, 260 nm, 280 nm). The purity ratios A260/A230 and A260/A280 and the DNA-concentration (according to the A260) were calculated. 50 μl of the undiluted eluates were used in a chromogenic LAL test (Associates of Cape Cod, Pyrochrome). Endotoxin concentrations were calculated according to the standard curves with the corresponding Control Standard Endotoxine (Associates of Cape Cod, CSE). The results are shown in table 6. The endotoxin concentration dependence of the used equilibration and wash buffers is shown in FIG. 5.

TABLE 6

The endotoxin concentration depends on the presence of the mixture of branched secondary alcohol ethoxylates. Unbranched secondary alcohol ethoxylates show no impact. oor = out of range of the standard curve. There is a clear effect of secondary branched alcohol ethoxylates on the endotoxin removal while unbranched secondary alcohol ethoxylates show an increased endotoxin concentration and little no effect of improvement as is obvious in diagram 2. The branched hydrophobic part shows unexpected advantages over a linear alkyl-chain of comparable length.

| Buffer | 15-S-7:TMN-6:TMN-10 | A260/A230 | | | A260/A280 | | | yield (DNA)/μg | | | EU/μg | | |
|---|---|---|---|---|---|---|---|---|---|---|---|---|---|
| 1 | 0.5:0:0 | 2.34 | 2.37 | 2.33 | 1.82 | 1.76 | 1.75 | 40 | 33 | 54 | oor | 0.698 | 0.454 |
|  |  |  | 2.35 |  |  | 1.78 |  |  | 42 |  |  | 0.576 |  |
| 2 | 0.5:0.4:0.1 | 2.37 | 2.35 | 2.33 | 1.82 | 1.82 | 1.82 | 37 | 47 | 50 | 0.027 | 0.029 | 0.019 |
|  |  |  | 2.35 |  |  | 1.82 |  |  | 45 |  |  | 0.025 |  |
| 3 | 0.4:0.4:0.1 | 2.35 | 2.35 | 2.37 | 1.83 | 1.83 | 1.81 | 48 | 43 | 45 | 0.017 | 0.028 | 0.032 |
|  |  |  | 2.36 |  |  | 1.82 |  |  | 45 |  |  | 0.026 |  |
| 4 | 0.3:0.4:0.1 | 2.37 | 2.39 | 2.35 | 1.77 | 1.79 | 1.80 | 47 | 45 | 43 | 0.024 | 0.039 | 0.047 |
|  |  |  | 2.37 |  |  | 1.79 |  |  | 45 |  |  | 0.037 |  |
| 5 | 0.2:0.4:0.1 | 2.35 | 2.37 | 2.34 | 1.80 | 1.86 | 1.79 | 44 | 46 | 46 | 0.031 | 0.138 | 0.035 |
|  |  |  | 2.35 |  |  | 1.82 |  |  | 45 |  |  | 0.068 |  |
| 6 | 0.1:0.4:0.1 | 2.38 | 2.35 | 2.36 | 1.79 | 1.80 | 1.76 | 43 | 40 | 40 | 0.021 | 0.023 | 0.079 |
|  |  |  | 2.36 |  |  | 1.78 |  |  | 41 |  |  | 0.041 |  |
| 7 | 0.0:0.4:0.1 | 2.33 | 2.36 | 2.34 | 1.77 | 1.82 | 1.82 | 44 | 46 | 46 | 0.055 | 0.032 | 0.043 |
|  |  |  | 2.34 |  |  | 1.80 |  |  | 45 |  |  | 0.043 |  |
| 8 | Triton ® X-114 | 2.33 | 2.35 | 2.35 | 1.89 | 1.80 | 1.77 | 44 | 43 | 47 | 0.450 | oor | 0.454 |
|  |  |  | 2.34 |  |  | 1.82 |  |  | 45 |  |  | 0.452 |  | columns with MAE-modified silica) including an extraction thimble were equilibrated with 15 ml of washing buffers according to table 7 in triplicate. The anion exchange columns were allowed to empty by gravity flow for all steps.

TABLE 7

Essential composition of the used washing (equilibration) buffers.

| Buffer | Detergent | Buffer | Salt |
|---|---|---|---|
| 1 | 0.4% Tergitol ® TMN-6, 0.1% Tegitol ® TMN-10 | 100 mM Tris, pH 6.5 | 0.8M KCl |
| 2 | 0.4% Tergitol ® TMN-6, 0.1% Tegitol ® TMN-10 | 100 mM Tris, pH 6.5 | 1.0M KCl |
| 3 | 0.4% Tergitol ® TMN-6, 0.1% Tegitol ® TMN-10 | 100 mM Tris, pH 6.5 | 1.2M KCl |

Example 4

*Escherichia coli* strain DH5α (Thermo Fisher Scientific) was transfected with the plasmid pcDNA™3.1 (+) (Thermo Fisher Scientific). The transfected cells were incubated overnight at 37° C. with constant shaking at 180 rpm in Cirglegrow™ medium (MP Biomedicals), containing 50 μg/ml Ampicillin (Sigma-Aldrich). Bacteria from 600 ml cell culture (absorption at 600 nm=12) were harvested by centrifugation at 5,000×g for 5 min at 4° C.

The bacterial cell pellet was resuspended in 100 ml resuspension buffer (50 mM Tris-Cl, pH 8.0, 10 mM EDTA, 100 μg/ml RNase A) by vigorous vortexing. To the homogeneous suspension, 150 ml lysis buffer (200 mM sodium hydroxide, 1% sodium dodecyl sulfate, 0.01% thymolphthaleine) were added and mixed with the resuspended cells by inverting the flask until a homogeneous, viscous lysate was obtained. The mixture was incubated for 5 minutes at room temperature (21° C.) before 100 ml neutralization buffer (3000 mM potassium acetate, 1000 mM sodium chloride, adjusted to pH 5) were added. The resulting mixture was inverted until a homogeneous off-white precipitate had formed and the color of the pH-indicator was completely reverted. The crude lysate was cleared by filtration with a Bottle Top Filter Type 1 (MACHEREY-NAGEL), yielding 390 ml of a cleared and pooled master-lysate. NucleoBond® Xtra Midi columns (MACHEREY-NAGEL, anion exchange TABLE 7-continued Essential composition of the used washing (equilibration) buffers.

| Buffer | Detergent | Buffer | Salt |
|---|---|---|---|
| 4 | 0.4% Tergitol ® TMN-6, 0.1% Tegitol ® TMN-10 | 100 mM Tris, pH 6.5 | 1.4M KCl |
| 5 | 0.5% Triton ® X-100 | 100 mM Tris, pH 6.5 | 1.2M KCl |
| 6 | 0.5% Triton ® X-114 | 100 mM Tris, pH 6.5 | 1.2M KCl |

Once the washing (equilibration) buffer had passed the column completely, 20.5 ml of the cleared lysate were added to each column. Following that loading step, the columns and filters were washed with each 5 ml of an extraction thimble flushing buffer (100 mM Tris, pH 6.5, 1.2 M KCl) after which the extraction thimble was discarded. The columns were washed succeedingly with 35 ml of the washing (equilibration) buffer according to table 7. Once the washing (equilibration) buffer had passed the column completely, 15 ml of a second washing buffer (100 mM Tris, pH 7.0, 1.2 M potassium chloride, 15% ethanol) were added to each column. Plasmid DNA was eluted by addition of 5 ml elution buffer (100 mM Tris, pH 9.0, 1.2 M potassium chloride, 15% isopropanol) to each column. The column flow through was collected individually for each column and precipitated by addition of 0.7 volumes isopropanol. The samples were mixed by vortexing, incubated for 2 min at room temperature (21° C.) and centrifuged at 4° C. for 15 min at 5,000×g. The supernatant was decanted and the DNA pellets washed with 2 ml of 70% ethanol each. After another centrifugation step (5 min with 5,000×g at 4° C.) the supernatant was decanted and the DNA pellet dried at room temperature. Once the ethanol was evaporated completely, each DNA pellet was redissolved in 200 μl endotoxin-free $H_2O$-EF (MACHEREY-NAGEL).

The redissolved DNA was measured photometrically (230 nm, 260 nm, 280 nm). The purity ratios A260/A230 and A260/A280 and the DNA-concentration (according to the A260) were calculated. 1 μl of the redissolved DNA was loaded onto a 1% TAE Agarose gel which was run for 60 min at 100 V. 50 μl of the undiluted eluates were used in a chromogenic LAL test (Associates of Cape Cod, Pyrochrome). Endotoxin concentrations were calculated according to the standard curves with the corresponding Control Standard Endotoxine (Associates of Cape Cod, CSE).

The photometric results are shown in Table 8 below. It is known in the art that the concentration of anions (here: chloride) is a relevant factor for the binding and elution of molecules from anion exchange matrices. Example 4 shows that the endotoxin removal effect is not due to an optimized potassium chloride concentration. There is no trend in endotoxin concentration or purity ratios as shown in table 8. A detectable effect might be a decrease in DNA yield which can be expected. The endotoxin concentration in EU/μg remains constant, indicating that there is no preferred removal of endotoxins or DNA by an increased chloride concentration.

TABLE 8

Analytical results of experiment 4. There is a decrease in yield with increasing concentrations of potassium chloride but no effect on the photometric purity ratios (A260/A280, A260/A230) or the endotoxin concentration.

| Buffer | c(KCl) | A260/A230 | | | A260/A280 | | | yield (DNA)/μg | | | EU/μg | | |
|---|---|---|---|---|---|---|---|---|---|---|---|---|---|
| 1 | 0.8M | 2.32 | 2.34 | 2.19 | 1.89 | 1.89 | 1.86 | 78 | 71 | 71 | 0.022 | 0.009 | 0.017 |
|   |   |   | 2.28 |   |   | 1.88 |   |   | 73 |   |   | 0.016 |   |
| 2 | 1.0M | 2.32 | 2.32 | 2.33 | 1.89 | 1.88 | 1.89 | 66 | 72 | 70 | 0.012 | 0.016 | 0.012 |
|   |   |   | 2.32 |   |   | 1.89 |   |   | 69 |   |   | 0.013 |   |
| 3 | 1.2M | 2.32 | 2.32 | 2.34 | 1.90 | 1.89 | 1.89 | 41 | 68 | 70 | 0.022 | 0.018 | 0.008 |
|   |   |   | 2.33 |   |   | 1.89 |   |   | 59 |   |   | 0.016 |   |
| 4 | 1.4M | 2.34 | 2.27 | 2.31 | 1.90 | 1.89 | 1.88 | 53 | 54 | 53 | 0.034 | 0.021 | 0.013 |
|   |   |   | 2.31 |   |   | 1.89 |   |   | 53 |   |   | 0.023 |   |
| 5 | Triton ® X-100 | 2.36 | 2.32 | 2.34 | 1.90 | 1.90 | 1.90 | 33 | 68 | 70 | 0.024 | 0.016 | 0.010 |
|   |   |   | 2.34 |   |   | 1.90 |   |   | 57 |   |   | 0.017 |   |
| 6 | Triton ® X-114 | 2.32 | 2.32 | 2.30 | 1.90 | 1.90 | 1.88 | 61 | 61 | 68 | 0.034 | 0.019 | 0.030 |
|   |   |   | 2.31 |   |   | 1.89 |   |   | 64 |   |   | 0.028 |   |

The invention claimed is:

1. A method for purifying or isolating plasmid DNA and reducing the endotoxin contamination thereof, which comprises
   (a) lysing bacterial cells containing the desired plasmid DNA;
   (b) clearing the cell lysate from cell debris and precipitated contaminants;
   (c) applying the cleared lysate to an anion exchange matrix, therewith binding DNA, endotoxins and other polyanions from the cleared lysate at least partially to the anion exchange matrix;
   (d) washing the anion exchange matrix with a non-turbid aqueous wash buffer solution comprising a detergent mixture with at least two different secondary branched alcohol ethoxylate detergents having different ethylene oxide (EO) chain lengths to remove endotoxins bound to the anion exchange matrix, wherein the two branched secondary alcohol ethoxylate detergents are compounds of the general formula (I)

wherein n represents the number of EO repetitions and is, independent from its occurrence in the other detergent, an integer from 6 to 15, while the difference of n in the at least two detergents is at least 2, wherein the amount (vol) of the secondary branched alcohol ethoxylate detergent with the shorter EO chain is greater than that of the secondary branched alcohol ethoxylate detergent with the longer EO chain and is in the range from 10:1 to 1.5:1;
   (e) eluting the plasmid DNA from the anion exchange matrix with an elution buffer.

2. The method of claim 1, wherein the method, prior to step (c), further comprises equilibrating the anion exchange matrix with an equilibration buffer comprising a detergent and/or an alcohol.

3. The method of claim 2, wherein said equilibration buffer comprises a detergent mixture with two different secondary branched alcohol ethoxylate detergents having different ethylene oxide chain length, wherein the two branched secondary alcohol ethoxylate detergents are compounds of the general formula (I)

wherein n represents the number of EO repetitions and is, independent from its occurrence in the other detergent, an integer from 6 to 15, while the difference of n in the at least two detergents is at least 2, wherein the amount (vol) of the secondary branched alcohol ethoxylate detergent with the shorter EO chain is greater than that of the secondary branched alcohol ethoxylate detergent with the longer EO chain and is in the range from 10:1 to 1.5:1.

4. The method of claim 1, wherein the difference of n in the at least two detergents is at least 3.

5. The method of claim 1, wherein one of the secondary branched alcohol ethoxylate detergents is a compound of the general formula (I) with n=8 and the other is a compound of the general formula (I) with n=11.

6. The method of claim 3, wherein, in the detergent mixture of the equilibration buffer, the ratio (v/v) of the detergent with a shorter EO chain to that with a longer EO chain is in the range from 5:1 to 2:1.

7. The method of claim 1, wherein in the detergent mixture of the wash buffer solution, the ratio (v/v) of the detergent with a shorter EO chain to that with a longer EO chain is in the range of 5:1 to 2:1.

8. The method of claim 6, wherein the detergent mixture is a combination of about 4 parts (vol) of the shorter chain detergent and 1 part (vol) of the longer chain detergent.

9. The method of claim 2, wherein the wash buffer solution and/or the equilibration buffer comprises the detergent mixture in a concentration of at least 0.1% (v/v).

10. The method of claim 9, wherein the wash buffer solution and/or the equilibration buffer comprises the detergent mixture in a concentration of at least 0.5% (v/v).

11. The method of claim 2, wherein the wash buffer solution and/or the equilibration buffer further comprises at least one salt in a concentration of at least 500 mM.

12. The method of claim 11, wherein said salt is selected from the group consisting of KCl, NaCl, LiCl, $CaCl_2$, $MgCl_2$, and the corresponding acetates.

13. The method of claim 2, wherein the wash buffer and/or the equilibration buffer further comprises at least a buffer substance in a concentration sufficient to stabilize the pH value.

14. The method of claim 13, wherein the buffer substance is selected from the group consisting of Tris, MOPS, Bis-Tris and phosphate.

15. The method of claim 2, wherein the wash buffer solution and/or the equilibration does not contain any organic solvents.

16. The method of claim 15, wherein the wash buffer solution and/or the equilibration buffer does not contain any ethanol.

17. The method of claim 2, wherein the equilibration buffer contains at least a buffer substance and is buffered to a pH which protonates the anion exchange groups of the anion exchange matrix.

18. The method of claim 17, wherein the buffer substance is selected from the group consisting of Tris, MOPS, Bis-Tris and phosphate.

19. The method of claim 1, wherein the method, after washing step (d), further comprises washing with a detergent-free aqueous wash buffer.

20. The method of claim 19, wherein said aqueous wash buffer solution comprises at least one salt and a buffer substance.

21. The method of claim 1, wherein the elution buffer comprises at least one salt and a buffer substance stabilizing an alkaline pH value.

22. The method of claim 1, which is for reducing endotoxin contamination in plasmid preparations.

23. A non-turbid aqueous wash buffer solution or an equilibration buffer solution comprising at least two different secondary branched alcohol ethoxylate detergents with different ethylene oxide (EO) chain lengths, wherein the two branched secondary alcohol ethoxylate detergents are compounds of the general formula (I)

(I)

wherein n represents the number of EO repetitions and is, independent from its occurrence in the other detergent, an integer from 6 to 15, while the difference of n in the at least two detergents is at least 2, wherein the amount (vol) of the secondary branched alcohol ethoxylate detergent with the shorter EO chain is greater than that of the secondary branched alcohol ethoxylate detergent with the longer EO chain and is in the range from 10:1 to 1.5:1.

24. A kit comprising the non-turbid aqueous wash buffer solution and/or the equilibration solution of claim 23.

25. The kit of claim 24, which comprises the aqueous wash buffer solution and the an equilibration buffer solution.

26. The kit of claim 24, which further comprises one or more of the components selected from the group consisting of (i) a detergent-free aqueous wash buffer comprising at least one salt and a buffer substance, (ii) an elution buffer comprising at least one salt and a buffer substance stabilizing an alkaline pH value, (iii) a lysis buffer, and (iv) an anion exchange matrix.

* * * * *